(12) United States Patent
Shukla

(10) Patent No.: US 7,746,974 B2
(45) Date of Patent: Jun. 29, 2010

(54) RADIOGRAPHIC AND FLUOROSCOPIC CT IMAGING

(75) Inventor: Himanshu P. Shukla, Lafayette, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/540,043

(22) Filed: Sep. 29, 2006

(65) Prior Publication Data

US 2008/0080662 A1  Apr. 3, 2008

(51) Int. Cl.
*A61B 6/00* (2006.01)

(52) U.S. Cl. .............................................. 378/4; 378/9

(58) Field of Classification Search ................ 378/4–20, 378/9, 134–136, 901
See application file for complete search history.

(56) References Cited

U.S. PATENT DOCUMENTS

| | | | | |
|---|---|---|---|---|
| 4,250,425 A * | 2/1981 | Gabbay et al. | ............... | 378/125 |
| 4,926,452 A * | 5/1990 | Baker et al. | ..................... | 378/22 |
| 5,173,852 A * | 12/1992 | Lonn | ............................. | 378/9 |
| 5,265,142 A * | 11/1993 | Hsieh | ............................. | 378/4 |
| 5,511,105 A * | 4/1996 | Knott | ......................... | 378/134 |
| 5,539,798 A * | 7/1996 | Asahina et al. | ............. | 378/98.5 |
| 5,590,164 A * | 12/1996 | Kawai et al. | .................... | 378/4 |
| 5,594,768 A * | 1/1997 | Fujii et al. | ..................... | 378/21 |
| 5,625,661 A * | 4/1997 | Oikawa | ........................ | 378/15 |
| 6,292,531 B1 * | 9/2001 | Hsieh | ........................... | 378/37 |
| 6,963,631 B2 * | 11/2005 | Brunnett | ..................... | 378/98.8 |
| 6,983,035 B2 * | 1/2006 | Price et al. | ................... | 378/124 |
| 7,187,748 B2 * | 3/2007 | Hoffman | ...................... | 378/15 |
| 7,187,756 B2 * | 3/2007 | Gohno et al. | ............... | 378/124 |
| 7,305,063 B2 * | 12/2007 | Heuscher | ..................... | 378/12 |
| 2003/0043957 A1 * | 3/2003 | Pelc | ............................... | 378/4 |
| 2005/0133706 A1 * | 6/2005 | Eberhard et al. | ............ | 250/234 |
| 2005/0195935 A1 * | 9/2005 | Yahata | ........................... | 378/4 |
| 2005/0238136 A1 * | 10/2005 | Bruder et al. | .................. | 378/9 |
| 2005/0243969 A1 * | 11/2005 | Andrews | ..................... | 378/119 |
| 2006/0215890 A1 * | 9/2006 | Dunham | ..................... | 382/128 |

OTHER PUBLICATIONS

Kyriakou et al., Impact of the z-flying focal spot on resolution and artifact behavior for a 64-slice spiral CT scanner, Computer Tomography, Eur. Radiol, Apr. 2006, pp. 1206-1215.*

Schardt et al., New x-ray tube performance in computed tomography by introducing the rotating envelope tube technology, Med Phys., 31 (9), Sep. 2004, pp. 2699-2706.*

(Continued)

*Primary Examiner*—Edward J Glick
*Assistant Examiner*—Alexander H Taningco

(57) ABSTRACT

A system includes emission of first electrons toward a first focal spot using an X-ray tube located at a first position, emission of first radiation from the first focal spot toward an object, acquisition of a first projection of the object based on the emitted first radiation using a computed tomography radiation detector, emission of second electrons toward a second focal spot using the X-ray tube located at the first position, emission of second radiation from the second focal spot toward the object, acquisition of a second projection of the object based on the emitted second radiation using the computed tomography radiation detector, and generation of an image of the object based on the first projection and the second projection.

7 Claims, 9 Drawing Sheets

OTHER PUBLICATIONS

Nikolaou et al, Advances in cardiac CT imaging: 64-slice scanner, The international journal of cardiovascular imaging, 20, 2004, pp. 535-540.*

Schroder et al., CT Detector know-how: How Ceramic and Electronics become Medical Technology, Medical Solutions, Jun. 2004, pp. 64-70.*

Flohr et al., Image reconstruction and image quality evaluation for a 64-slice CT scanner with z-flying focal spot, Med. Phys., 32, Aug. 8, 2005, pp. 2536-2547.*

Flohr, T.G. et al., "Image reconstruction and image quality evaluation for a 64-slice CT scanner with z-flying focal spot", Medical Physics, vol. 32, No. 8, Aug. 2005, © 2005 Am. Assoc. Phys. Med.

* cited by examiner

RADIOGRAPHIC AND FLUOROSCOPIC CT IMAGING

BACKGROUND

1. Field

The embodiments described below relate generally to imaging using X-rays. More particularly, some embodiments concern two-dimensional imaging using a computed tomography scanner.

2. Description

Images of internal patient volumes are commonly used in modern medical practice. Such images may be used to generate or confirm a diagnosis and/or to plan a course of treatment.

In order to obtain an internal image, a patient is typically transferred to a facility (i.e., an "RF" room) providing radiographic/fluoroscopic imaging. The RF room includes one or more monolithic systems for obtaining two-dimensional (radiographic) images and/or two-dimensional+time (fluoroscopic) images. In some instances, these images may be sufficient for diagnosis, intervention, and treatment planning.

In other instances, the images obtained in the RF room may indicate a volume within the patient about which more information is desired. Accordingly, the patient may be moved to a three-dimensional imaging system located in another room or building. The three-dimensional imaging system may comprise a computed tomography ("CT") system including an X-ray source and a radiation receiver that are mounted to face one another on opposite sides of a ring. The patient is positioned within the ring so that the volume of interest lies between the X-ray source and the radiation receiver. A three-dimensional image of the volume of interest is generated from two-dimensional projection images obtained by the receiver as the ring is rotated.

Two-dimensional images are initially acquired in the RF room for at least two reasons. First, the significant cost of obtaining a three-dimensional image may be avoided if the images acquired in the RF room are sufficient for their intended purpose. Second, high resolution two-dimensional images acquired in the RF room are frequently sufficient for the clinical task. It has been proposed to use two-dimensional projection images acquired by a CT scanner as an alternative to RF room images, but currently these projection images are not sufficiently detailed for most diagnosis and/or treatment planning.

Systems are desired that may reduce the need for separate RF and CT imaging systems.

SUMMARY

To address at least the foregoing, some embodiments provide a system, method, apparatus, and means to emit first electrons toward a first focal spot using an X-ray tube located at a first position, to emit first radiation from the first focal spot toward an object, to acquire a first projection of the object based on the emitted first radiation using a computed tomography radiation detector, to emit second electrons toward a second focal spot using the X-ray tube located at the first position, to emit second radiation from the second focal spot toward the object, to acquire a second projection of the object based on the emitted second radiation using the computed tomography radiation detector, and to generate an image of the object based on the first projection and the second projection.

In further aspects, a focal spot associated with the X-ray tube is moved in a first direction from the first focal spot to a second focal spot, the object is moved relative to the X-ray tube in a second direction perpendicular to the first direction, third radiation is emitted from the first focal spot toward the moved object using the X-ray tube located at the first position, a third projection of the moved object is acquired based on the emitted third radiation using the computed tomography radiation detector, fourth radiation is emitted from the second focal spot toward the moved object using the X-ray tube located at the first position, and a fourth projection of the moved object is acquired based on the emitted fourth radiation using the computed tomography radiation detector. The image of the object is generated based on the first projection, the second projection, the third projection and the fourth projection.

Alternatively to the previous aspect, third radiation may be emitted toward the object from a third focal spot using the X-ray tube located at the first position, and a third projection of the object may be acquired based on the emitted third radiation using a computed tomography radiation detector, wherein the image of the object is generated based on the first projection, the second projection and the third projection.

In some aspects, a two-dimensional image of the object is acquired, the image is superimposed on a portion of the two-dimensional image, the image is updated, and the updated image is superimposed on the portion of the two-dimensional image.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated by for carrying out some embodiments. Various modifications, however, will remain readily apparent to those in the art.

Figure 1:
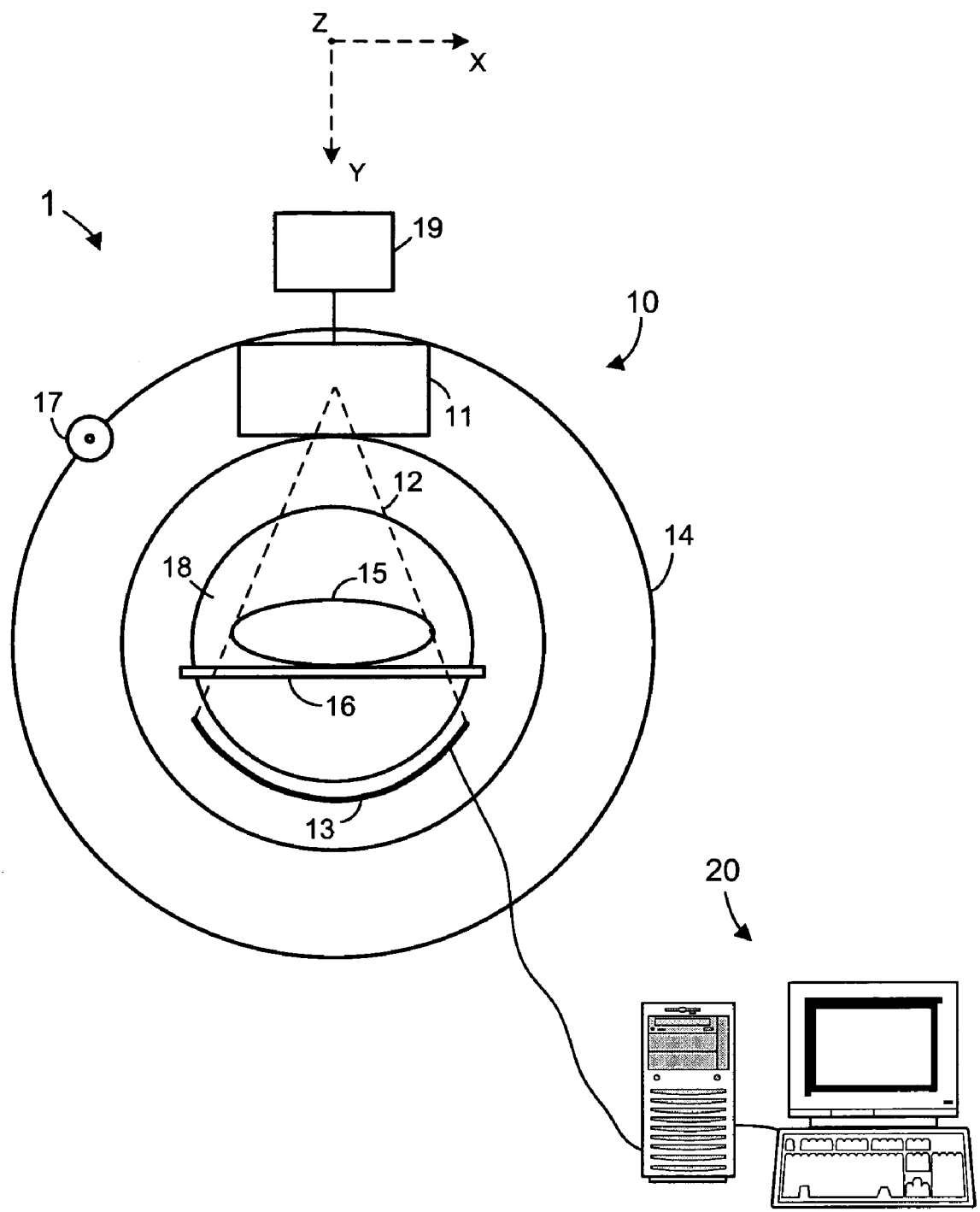
FIG. 1 is a diagram illustrating a computed tomography system according to some embodiments.

FIG. 1 illustrates CT system 1 according to some embodiments. CT system 1 comprises CT scanner 10 and computer system 20. In some embodiments, CT system 1 operates to efficiently generate a two-dimensional image having improved resolution over conventional CT projection images.

CT scanner 10 comprises X-ray tube 11 for emitting fan-shaped X-ray beam 12 toward CT radiation detector 13. X-ray tube 11 may comprise any suitable X-ray tube and detector 13 may comprise any suitable detector, including but not limited to a collimated multi-detector device. Detector 13 may comprise one or more rows of individual detecting elements, with each row being roughly aligned with the illustrated X-direction.

Both X-ray tube 11 and radiation detector 13 are mounted on ring 14 such that they may be rotated through 360 degrees while maintaining the physical relationship therebetween. Such rotation facilitates the acquisition of projection images used to generate three-dimensional images. However, X-ray tube 11 may remain at a fixed position during the acquisition of projections which are used to generate a two-dimensional image according to some embodiments.

In conventional operation, object 15 (e.g., a human body) is positioned on table 16 to place a portion of body 15 between X-ray tube 11 and radiation detector 13. Next, X-ray tube 11 and detector 13 are rotated by rotation drive 17 around cavity 18 in which object 15 lies. During this rotation, X-ray tube 11 is powered by high-voltage generator 19 to transmit X-ray radiation toward detector 13. Detector 13 receives the radiation and produces a projection image for each projection angle.

Each projection image comprises a set of data that represents the attenuative properties of tissues along divergent lines between X-ray tube 11 and detector 13. The projection images are transmitted to computer system 20. For conventional generation of a three-dimensional image, computer system 20 calculates attenuation coefficients (e.g., Hounsfield numbers) of predetermined points based on the projection images. The attenuation coefficients are used to generate a three-dimensional image representing the portion of object 15 that lies between X-ray tube 11 and radiation detector 13.

The dimensions of the projection images are similar to the dimensions of detector 13 on which detecting elements reside. Referring to the FIG. 1 example, the dimension on which the detecting elements reside in the illustrated X-direction may be sufficient to capture most of radiation 12 that passes through object 15 in the X-direction. Detector 13 may comprise only a few (e.g., one through five) rows of detecting elements in the illustrated Z-direction (i.e., into and out of the plane of FIG. 1). Accordingly, the acquired projection images and resulting three-dimensional image may extend only a few centimeters in the Z-direction.

Table 16 may be moved in the Z-direction to place a different portion of object 15 between X-ray tube 11 and radiation detector 13. A three-dimensional image of the different portion may be acquired as described above. This image may be combined with the above-mentioned three-dimensional image to generate a single three-dimensional image of both portions that is longer in the Z-direction than either of the two three-dimensional images of which it is composed.

According to some embodiments, X-ray tube 11 emits first electrons toward a first focal spot on a target while located at a first X,Y,Z position, and first radiation is emitted from the first focal spot towards object 15 due to electron collisions with the target. X-ray tube 11 may, for example, comprise an X-ray tube for generating photon radiation having energies in the 50 to 250 keV range and including a cathode and an anode. The first electrons may be emitted from the cathode and the first focal spot may be located on the anode.

Detector 13 may acquire a first projection of object 15 based on the emitted first radiation. In some embodiments, the emitted first radiation is collimated prior to reaching object 15. X-ray tube 11 may then emit second electrons toward a second focal spot while X-ray tube 11 is still located at the first position. In this regard, CT system 1 may include any system for controlling a location of a focal spot associated with X-ray tube 11 that is or becomes known. Second radiation is emitted from the second focal spot towards object 15.

Detector 13 acquires a second projection of object 15 based on the emitted second radiation, and generates an image of object 15 based on the first projection and the second projection. As mentioned above, the two-dimensional image may exhibit improved resolution over conventional CT projections. In some embodiments, the resolution is improved in the direction of movement of the focal spot. The foregoing example may be performed by elements of CT scanner 10 and computer system 20 working in concert.

Figure 2:
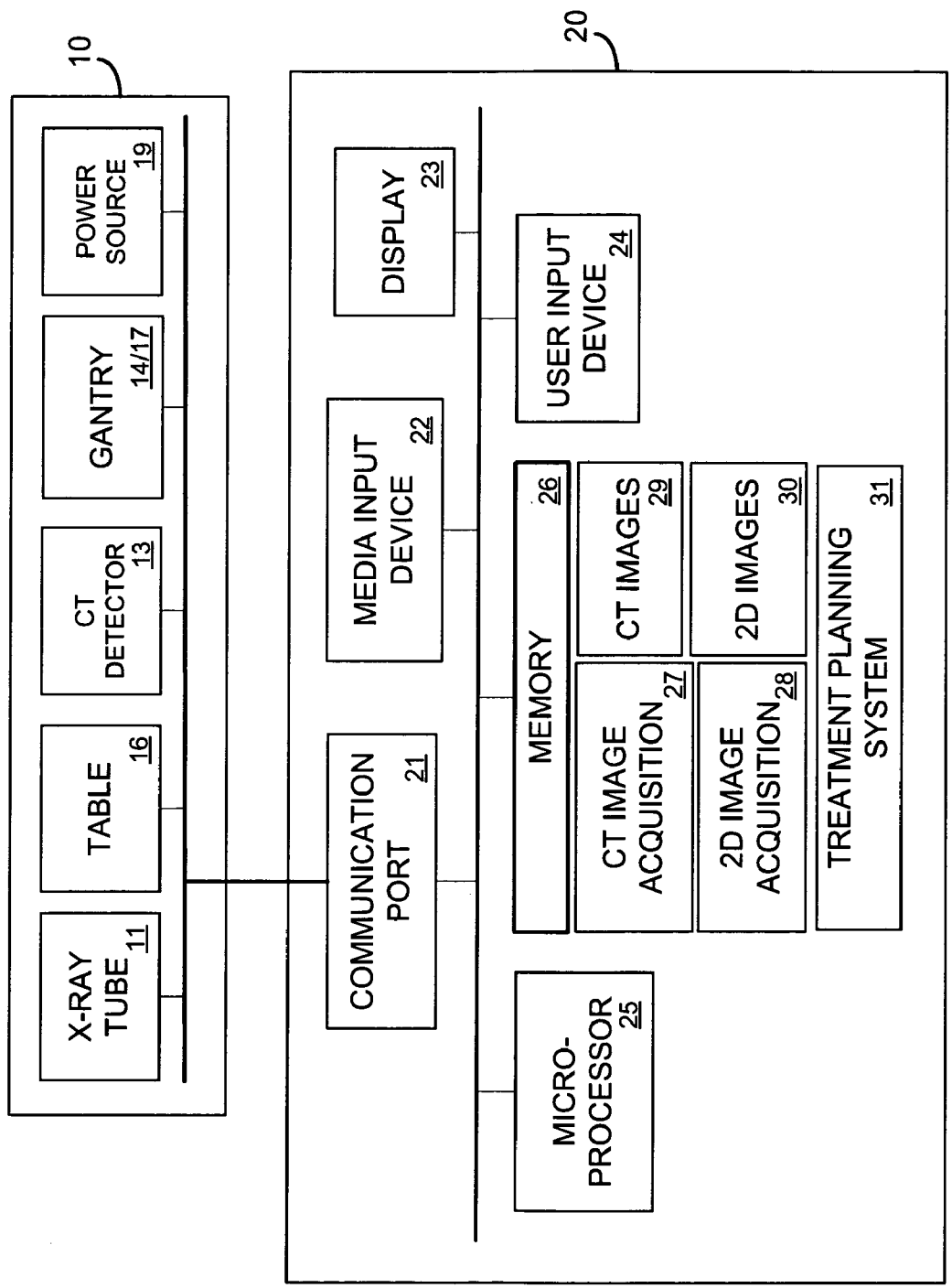
FIG. 2 is a block diagram illustrating elements of a computed tomography system according to some embodiments.

FIG. 2 is a block diagram of CT system 1 according to some embodiments. The illustrated elements may be implemented by any suitable combination of hardware, software and/or firmware.

Computer system 20 includes communication port 21 for interfacing with CT scanner 10. More particularly, computer system 20 may issue commands for controlling various elements of CT scanner 10 and may receive feedback therefrom via communication port 21. Computer system 20, may, for example, issue a command over communication port 21 to control X-ray tube 11 in order to move the focal spot thereof and CT detector 13 to acquire a first projection and a second projection as described above, and may receive the first projection and the second projection from CT scanner 10 over communication port 21.

Communication port 21 may comprise any type of interface suitable for receiving data from computer system 20. Communication port 21 may comprise a proprietary interface associated with a manufacturer of CT scanner 10. Computer system 20 also includes media input device 22 that may comprise a CD-ROM drive, a ZIP drive, a USB drive and/or any device for receiving a storage medium and reading data from the medium.

Display 23 may comprise any one or more devices for displaying images and control interfaces to a user. Display 23 may display images such as any projections and two-dimensional images acquired or generated and/or any fluoroscopic images generated according to some embodiments. User input device 24 may be operated by the user to input data and commands to computer system 20. User input device 24 may comprise any input device or devices that are or become known.

Microprocessor 25 executes processor-executable process steps stored in memory 26 to provide operation of CT system 1 according to some embodiments. In this regard, memory 26 may store process steps that are executable by microprocessor 25. These process steps may comprise CT image acquisition program 27 to provide conventional acquisition of projections and two-dimensional image acquisition program 28 to provide two-dimensional and/or two-dimensional+time images according to some embodiments. Memory 26 may also comprise CT images 29 and two-dimensional images 30 generated in conjunction with the foregoing process steps.

Memory 26 may, in some embodiments, include process steps of treatment planning system 31 to determine a treatment plan based on the acquired images. According to some embodiments, treatment planning system 31 may provide manipulation and enhancement of stored images to facilitate diagnosis and/or treatment planning.

A hardware environment according to some embodiments may include less or more elements than those shown in FIGS. 1 and 2. In addition, embodiments are not limited to the devices and/or to the illustrated environment. For example, some embodiments include another type of image acquisition device to acquire projections.

Figure 3:
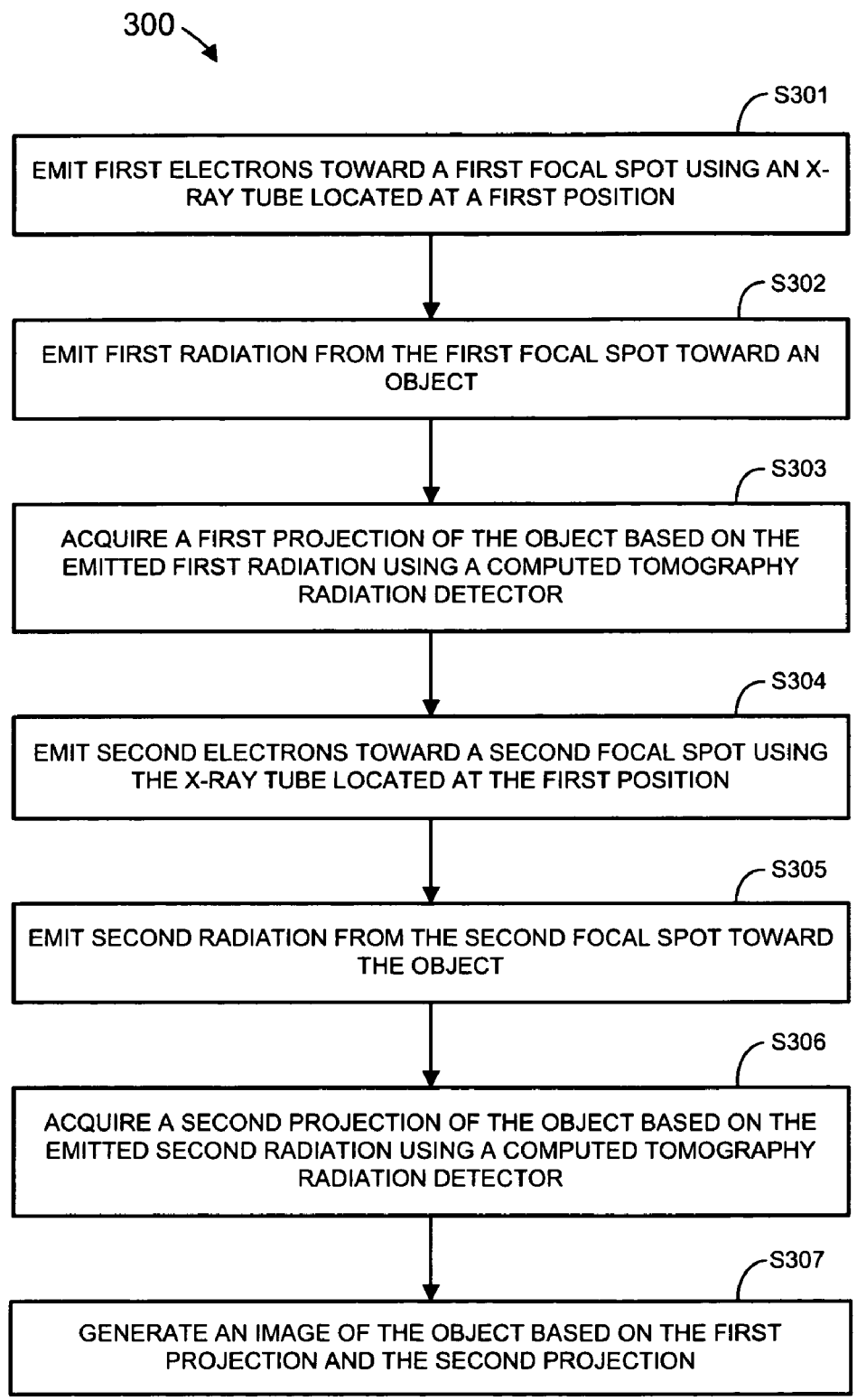
FIG. 3 comprises a flow diagram illustrating process steps according to some embodiments.

FIG. 3 is a flow diagram of process steps 300 executed by system 1 according to some embodiments. Process steps 300 may be embodied, in whole or in part, by hardware of and/or software executed by elements including but not limited to those of CT scanner 10 and computer system 20. Software embodying process steps 300 may be stored by any medium residing anywhere in CT system 1, including a fixed disk, a floppy disk, a CD-ROM, a DVD-ROM, a Zip™ disk, a magnetic tape, or a signal. Some or all of such software may also be stored in one or more devices.

Initially, at step S301, first electrons are emitted toward a first focal spot using an X-ray tube located at a first position. The first position depends upon the desired perspective of an image resulting from process 300. For example, X-ray tube 11 is positioned as shown in FIG. 1 if the object (e.g., a patient) lies face up on table 16 and if an anterior-to-posterior view is desired. The first position will be considered any position in three-dimensional space and will be represented by coordinates (x,y,z) of the coordinate system shown in FIG. 1.

Figure 4A:
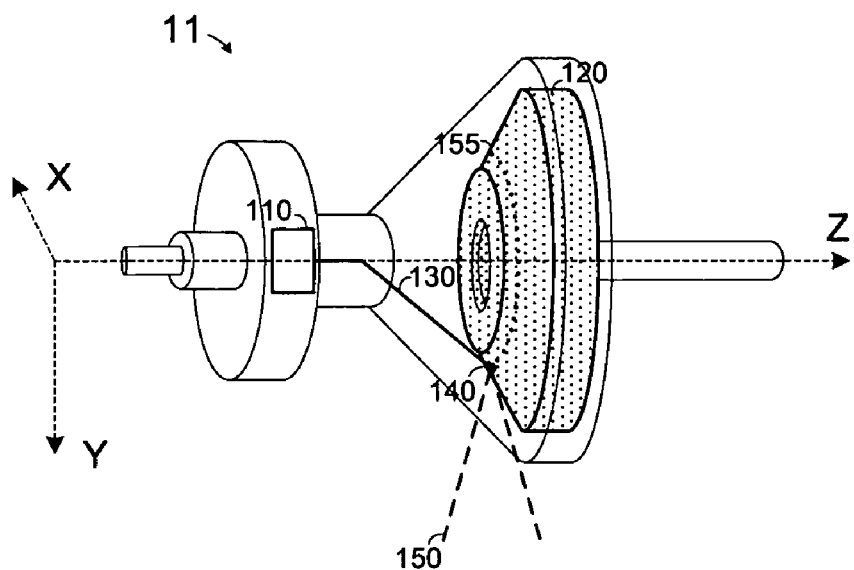
FIG. 4A is a representation of radiation emission from a first focal spot according to some embodiments.

FIG. 4A illustrates emission of first electrons toward a first focal spot according to some embodiments of step S301. According to the illustrated example, X-ray tube 11 comprises cathode 110 and anode 120. Cathode 110 emits high energy electrons 130, which may be steered toward first focal spot 140 of anode 120 using any systems that are or become known (e.g. deflector plates).

First radiation is emitted from the first focal spot at step S302. With reference to the example of FIG. 4A, collisions of electrons 130 with focal spot 140 may cause divergent X-ray radiation 150 to be emitted from focal spot 140 toward an object. Anode 120 of the illustrated embodiment is beveled to promote escape of X-rays 150 rather than attenuation and/or reabsorption thereof by anode 120. Anode 120 may rotate about the Z-axis while electrons 130 are aimed as shown, resulting in the impact of electrons 130 at various locations of anode 120 represented by dotted line 155. Despite this rotation, the (x,y,z) coordinate of first focal spot 140 may remain substantially stationary.

Returning to process 300, a first projection of the object is acquired based on the emitted first radiation at step S303. The first projection is acquired by a CT radiation detector. In some embodiments of step S303, CT detector 13 may receive radiation 150 after radiation 150 is collimated and then passes through body 15. The received radiation provides information regarding attenuative properties of the structures through which it has passed. Accordingly, CT detector 13 may acquire a projection of these structures based on the received radiation.

Figure 4B:
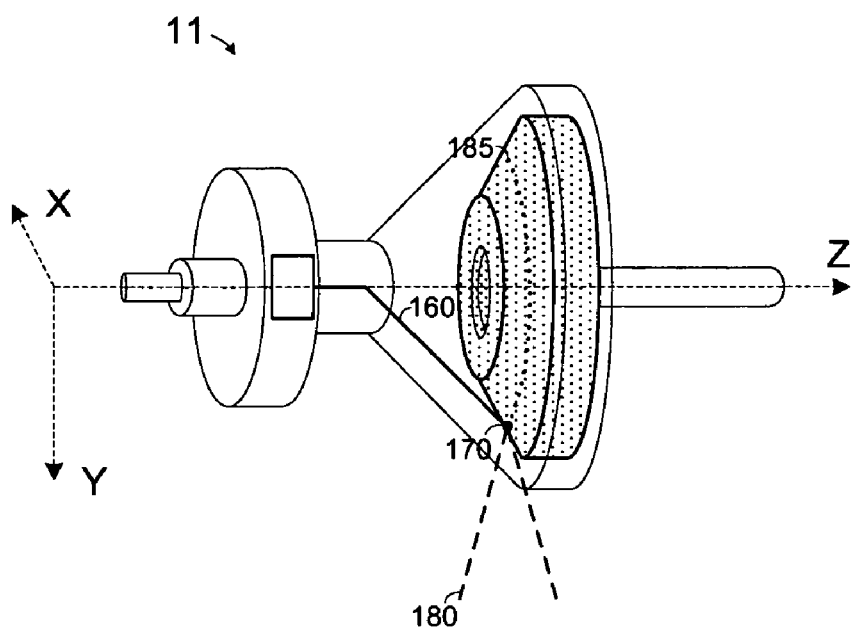
FIG. 4B is a representation of radiation emission from a second focal spot according to some embodiments.

Next, at step S304, the X-ray tube emits second electrons toward a second focal spot while the X-ray tube is located at the first position. FIG. 4B shows electrons 160 being steered toward second focal spot 170 of anode 120 according to some embodiments of step S304. As described above, the second electrons cause emission of second radiation from the second focal spot and towards the object at step S305.

As an example of step S305, FIG. 4B shows divergent X-ray radiation 180 being emitted from focal spot 170. As described with respect to FIG. 4A, electrons 160 may impact spinning anode 120 at various locations represented by dotted line 185, which exhibits a greater diameter than dotted line 155 due to the beveled geometry of anode 120. However, the (x,y,z) coordinate of second focal spot 170 may remain substantially stationary during this rotation.

A second projection of the object is acquired based on the emitted second radiation at step S306. CT detector 13 may acquire the second projection by receiving radiation 180 having passed through body 15 and by converting the spatial intensity distribution of the received radiation to image pixel values.

An image is generated at step S307 based on the first projection and on the second projection. The image may be generated using any suitable image processing algorithm for combining two projections. In some embodiments, computer system 20 receives the first projection and the second projection and performs image processing thereon to generate the image at step S307.

According to some embodiments, movement of the focal spot in a given direction improves image sampling with respect to the direction. The example of FIGS. 4A and 4B illustrates movement of the focal spot primarily in the Z-direction due to the beveled geometry of anode 120. Consequently, the resolution of the generated image may be improved in the Z-direction.

Figure 5A:
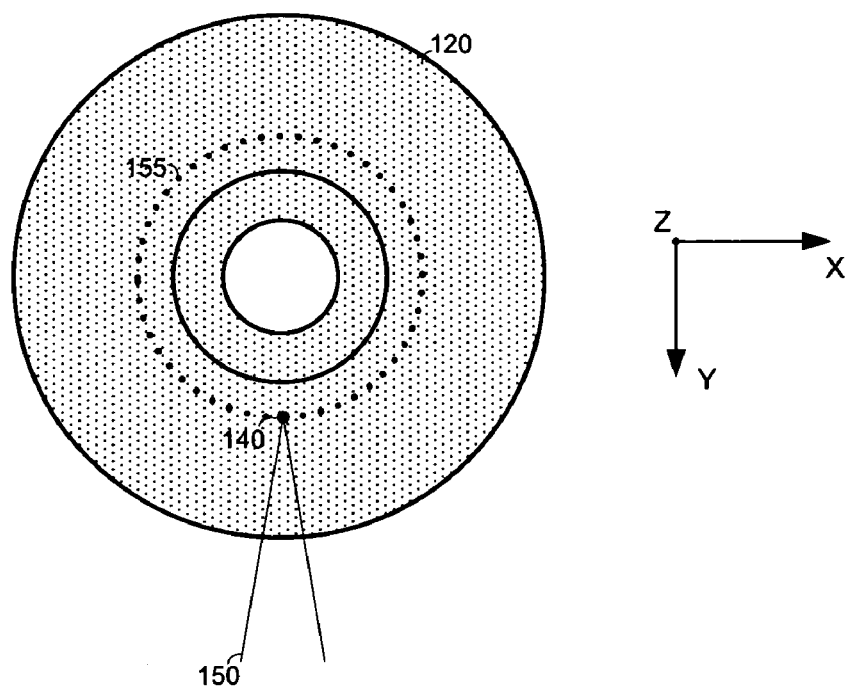
FIG. 5A is a representation of radiation emission from the first focal spot according to some embodiments.
Figure 5B:
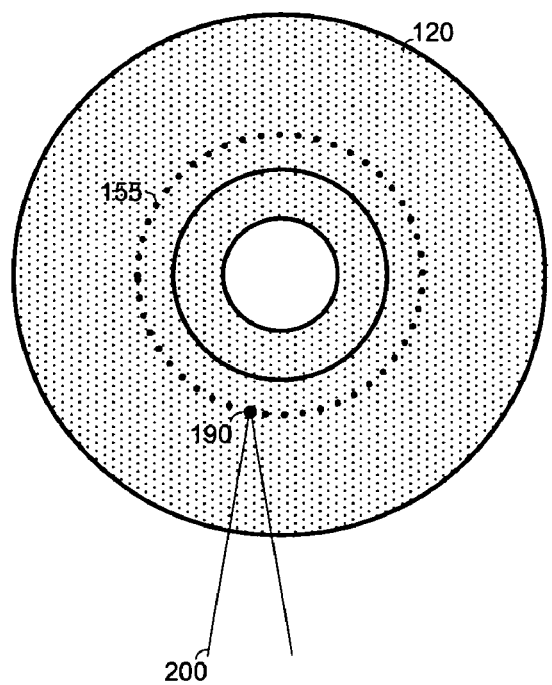
FIG. 5B is a representation of radiation emission from a third focal spot according to some embodiments.

FIGS. 5A and 5B illustrate movement of a focal spot in primarily an X-direction according to some embodiments. More specifically, FIG. 5A shows a front perspective view of anode 120, focal spot 140, radiation 150 and dotted line 155 of FIG. 4A. FIG. 5B illustrates emission of second electrons toward a second focal spot according to some embodiments of step S304.

Second focal spot 190 is also located on dotted line 155, but is shifted primarily in the X-direction. As a result, the Z-position of focal spot 190 is substantially identical to the Z-position of focal spot 140. Radiation 200 is emitted from focal spot 190 and a second projection may be acquired based thereon at step S306. According to the embodiment of FIGS. 5A and 5B, the resolution of the generated image may be improved in the X-direction.

Figure 6:
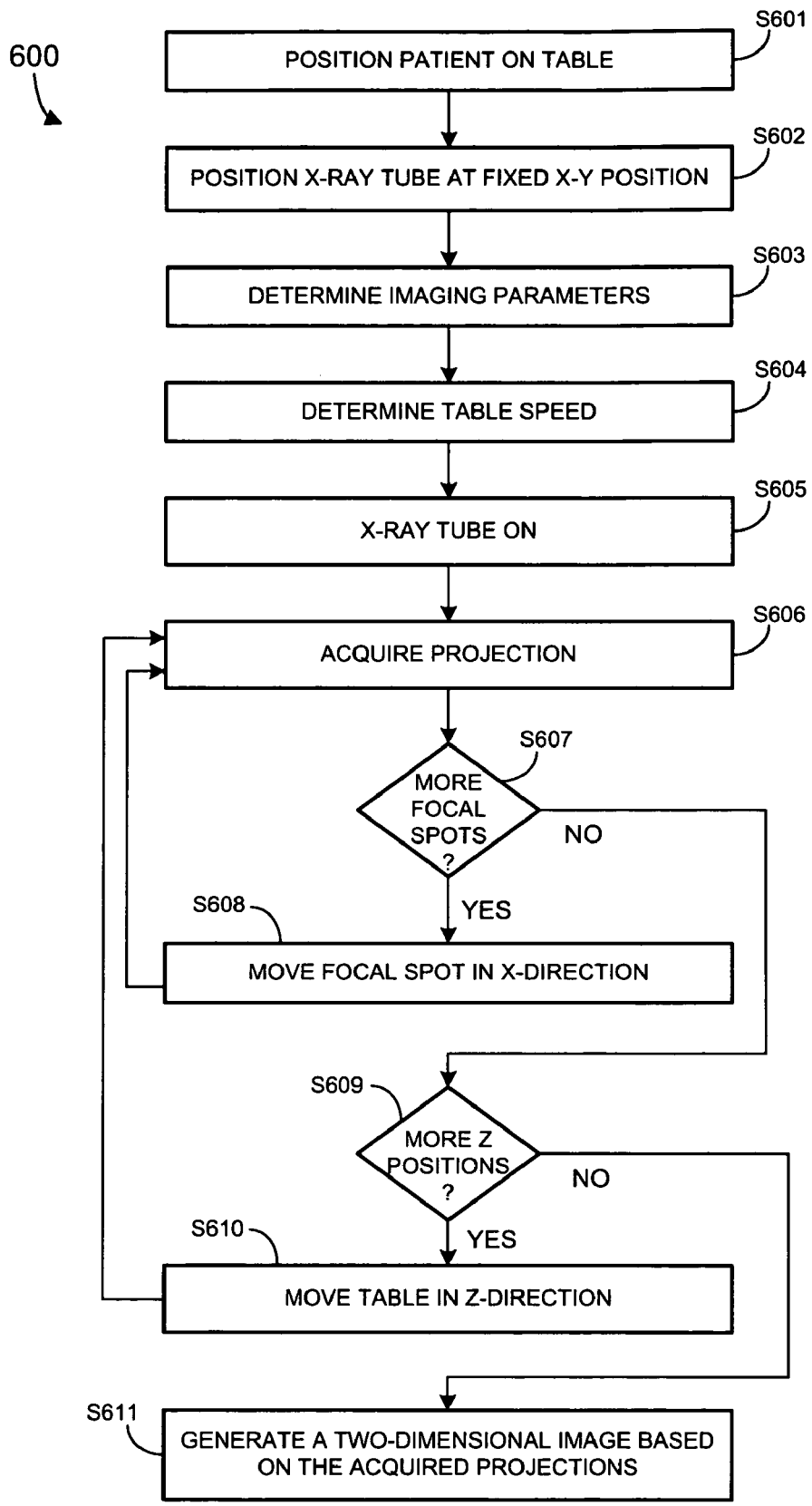
FIG. 6 comprises a flow diagram illustrating process steps according to some embodiments.

FIG. 6 is a flow diagram of process steps 600 executed by system 1 according to some embodiments. Process steps 600 may embody process steps 300 and may be embodied and/or implemented in any currently- or hereafter-known manner.

A patient is positioned on a table at step S601. The patient is positioned in accordance with the desired image perspective and such that a volume of interest resides between an X-ray tube and an X-ray detector. Image perspective may also or alternatively be controlled at step S602, in which the X-ray tube is positioned at a fixed position in the X-Y plane.

An X-Y plane according to some embodiments is illustrated in FIG. 1. For purposes of the present example, it will be assumed that X-ray tube 11 is positioned 90 degrees from the position illustrated in FIG. 1. This positioning may be accomplished by rotating ring 14 90 degrees. Assuming that object 15 is a patient lying face up on table 16, the resulting projection will depict a lateral view.

Suitable imaging parameters are determined at step S603. Possible imaging parameters according to some embodiments include, but are not limited to, source projection angle, X/Z planar resolution, longitudinal coverage, X-direction sampling rate, and Z-direction sampling rate. In some embodiments, the aforementioned sampling rates are based on the point spread function (PSF) of the subject imaging system. As is known in the art, the PSF may be determined based on lateral and longitudinal detector resolution, focal spot size and modulation, and other parameters. Any suitable methods for determining appropriate imaging parameters may be employed at step S603.

A table speed is determined at step S604. The determined table speed may refer to a speed at which object 15 moves relative to X-ray tube 11 and detector 13 in the Z-direction. The table speed may be computed based on the above-determined X-direction and Z-direction sampling rates.

Next, at step S605, the X-ray tube is turned on. The X-ray tube is turned on at step S605 to emit radiation exhibiting the imaging parameters determined at step S603. In this regard, the radiation is emitted from a first focal spot associated with the X-ray tube. A projection is then acquired based on at step S606. The projection may be acquired by a CT radiation detector, and comprises pixel values associated with structures through which the emitted radiation has passed.

At step S607, it is determined whether any additional focal spots are to be employed. Such a determination may be based on the determined imaging parameters, on capabilities of the system executing process 600, or on any other measure. According to the present example, three focal spots are to be used for image acquisition.

The focal spot is moved in the X-direction at step S608 after acquisition of the first projection, and a second projection is acquired at step S606. According to some embodiments, the focal spot is moved in the X-direction as described above with respect to FIG. 5B and the second projection is acquired based on radiation 200. In the present example, flow again cycles through steps S607, S608 and S606 to move the focal spot in the X-direction to a third focal spot and to acquire a third projection. Referring to FIG. 5B, the third focal spot may be located to the left of or to the right of focal spot 190.

Flow then proceeds from step S607 to step S609 after acquisition of the third projection. At step S609, it is determined whether additional Z positions are desired. For example, the Z dimension of each of the first, second and third projection is substantially equal to the Z dimension of the CT detector's detecting surface. If the longitudinal coverage determined at step S603 is greater than this Z dimension, it is determined at step S609 that more Z positions are desired.

The table is moved at step S610 to move the patient relative to the X-ray tube in the Z-direction. Flow then returns to step S606 to begin acquisition of three new projections using the three focal spots while a different portion of the patient is disposed between the X-ray tube and the CT detector.

Figure 7:
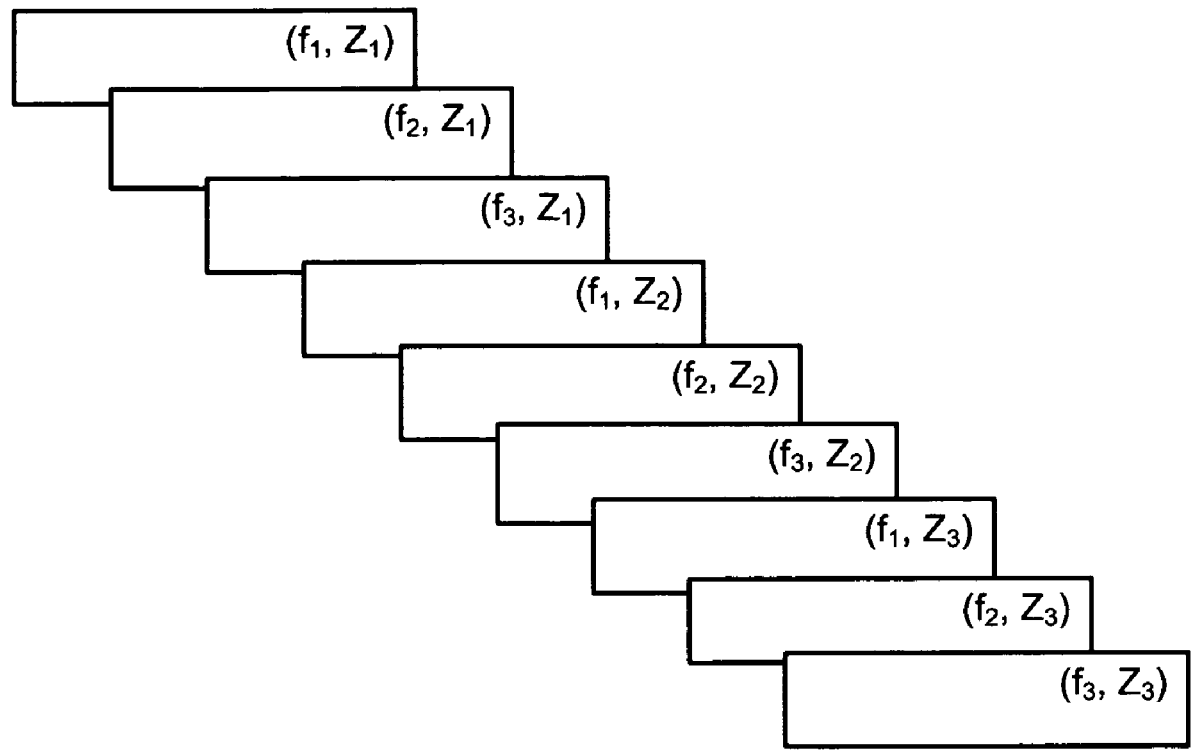
FIG. 7 comprises representations of two-dimensional images acquired according to some embodiments.

FIG. 7 depicts nine projections acquired during nine different iterations of step S606 according to the present example. The timing of the iterations is based upon the predetermined X and Z sampling rates. Each projection is labeled with the Z position and the focal spot associated with its acquisition. Assuming that only three Z positions are desired, flow proceeds from step S609 to step S611 to generate a two-dimensional image based on the nine projections of FIG. 7.

The acquired projections are combined into a single two-dimensional image at step S611. Step S611 may also comprise deconvolving the projections along the X-direction and/or Z-direction to remove blur according to known protocols. In this regard, any suitable post-processing may be implemented on the acquired projections and/or the image generated at step S611.

According to some embodiments of process 600, the focal spot is moved in the Z-direction instead of the X-direction at step S608. Generally, the focal spot may be moved in any direction in which improved sampling is desired. Some embodiments may provide, for each table position, movement of the focal spot in the X-direction to one or more locations and/or movement of the focal spot in the Z-direction to one or more locations, as well as acquisition of projections corresponding to each focal spot location. Each of these acquired projections may be used to generate a two-dimensional image at step S611.

The image generated at step S611 may exhibit a resolution suitable for diagnosis or treatment planning. Accordingly, a doctor or technician may analyze the image after step S611 to determine a course of action with respect to the patient. The course of action may include generating another two-dimensional image using process 600, performing a conventional CT scan, and/or generating a fluoroscopic image using a process such as process 800 of FIG. 8.

Figure 8:
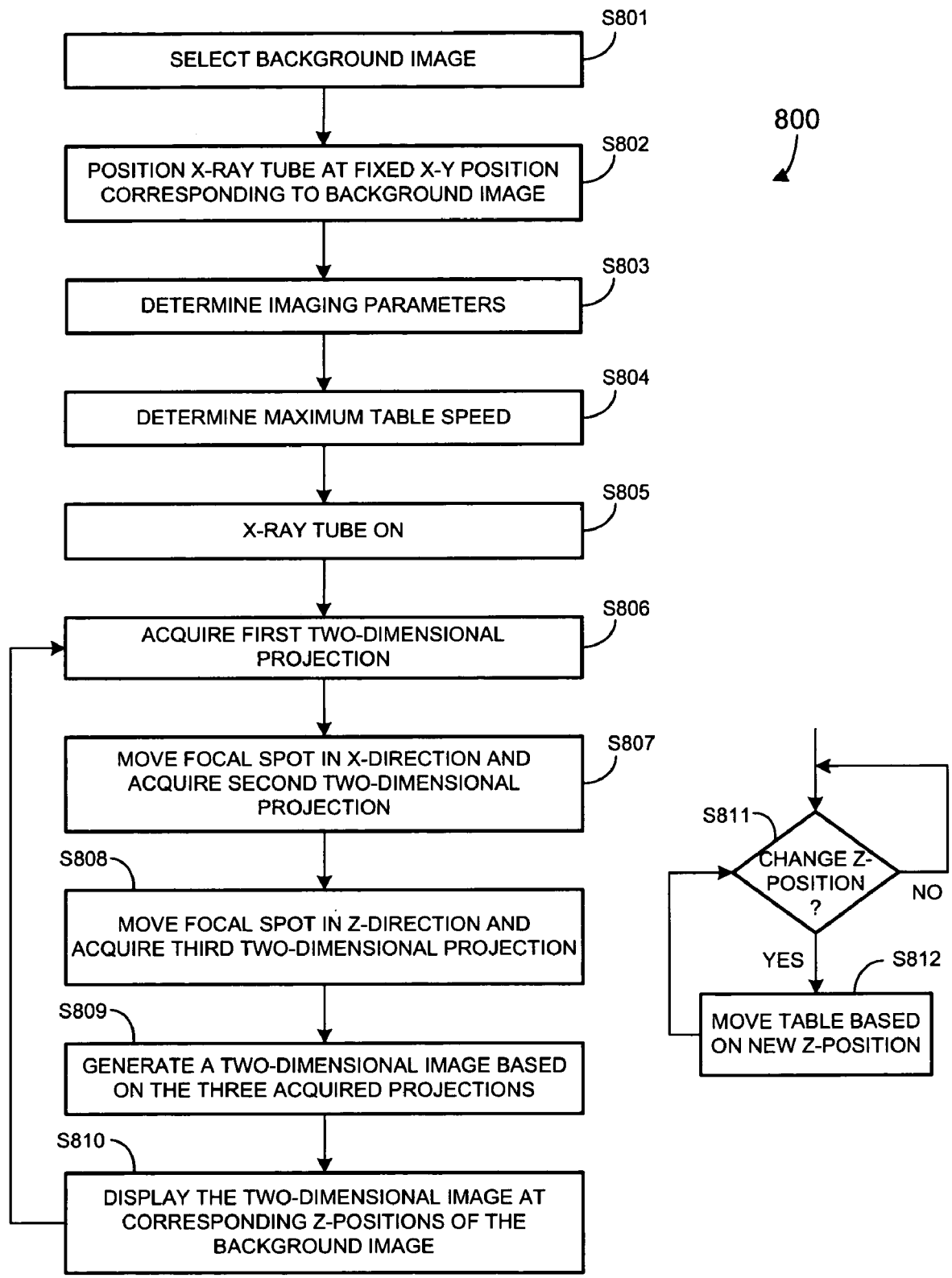
FIG. 8 comprises a flow diagram illustrating process steps according to some embodiments.

FIG. 8 is a flow diagram of process steps 800 executed by system 1 according to some embodiments. Process steps 800 may embody process steps 300 and may be embodied and/or implemented in any currently- or hereafter-known manner.

A background image is selected at step S801. The background image may comprise any two-dimensional image having a desired perspective. The background image may be modified to a desired scaled if necessary. In some embodiments, the selected background image is generated at step S611 of process 600.

Next, at step S802, an X-ray tube is positioned at a fixed X-Y position corresponding to the background image. For example, the X-ray tube may be positioned as shown in FIG. 1 if object 15 lies face up and the selected background image presents an anterior-posterior view.

Steps S803 and S805 may proceed as described above with respect to steps S603 and S605 of process 600 according to some embodiments. Some embodiments of step S804, however, comprise determining a maximum allowable table speed. In this regard, process 800 allows a user to move a table manually or remotely (e.g. using a joystick) in order to change the patient portion of which a fluoroscopic image is obtained. A maximum speed of this table movement is determined in step S804.

Process 800 assumes that two-dimensional projections will be acquired using three different focal spots that differ in X and/or Z position. In particular, a first two-dimensional projection is acquired at step S806. The first two-dimensional projection may be acquired by emitting radiation 150 from focal spot 140 of FIGS. 4A and 5A and receiving attenuated radiation 150 at detector 13. Detector 13 may be two or more detecting elements wide in the Z-direction in order to enable acquisition of a two-dimensional projection.

The focal spot is moved in the X-direction and a second two-dimensional projection is acquired at step S807. Continuing with the current example, the focal spot may be moved in some embodiments of step S807 as shown in FIG. 5B. Accordingly, the second two-dimensional projection is acquired based on radiation 200.

Next, at step S808, the focal spot is moved in the Z-direction and a third two-dimensional projection is acquired. FIG. 4B illustrates movement of the focal spot in the Z-direction to focal spot 170 according to some embodiments of step S808. The third two-dimensional projection is therefore acquired based on radiation 180.

A two-dimensional image may be generated at step S809 based on the three acquired projections as described with respect to step S611. Each of the three two-dimensional projections spans a same range of Z-positions since neither the X-ray tube nor the acquiring detector moves in the Z-direction. The generated two-dimensional image also spans the above-mentioned range of Z-positions. Accordingly, the generated two-dimensional image is displayed at step S810 at corresponding Z positions of the background image.

Figure 9:
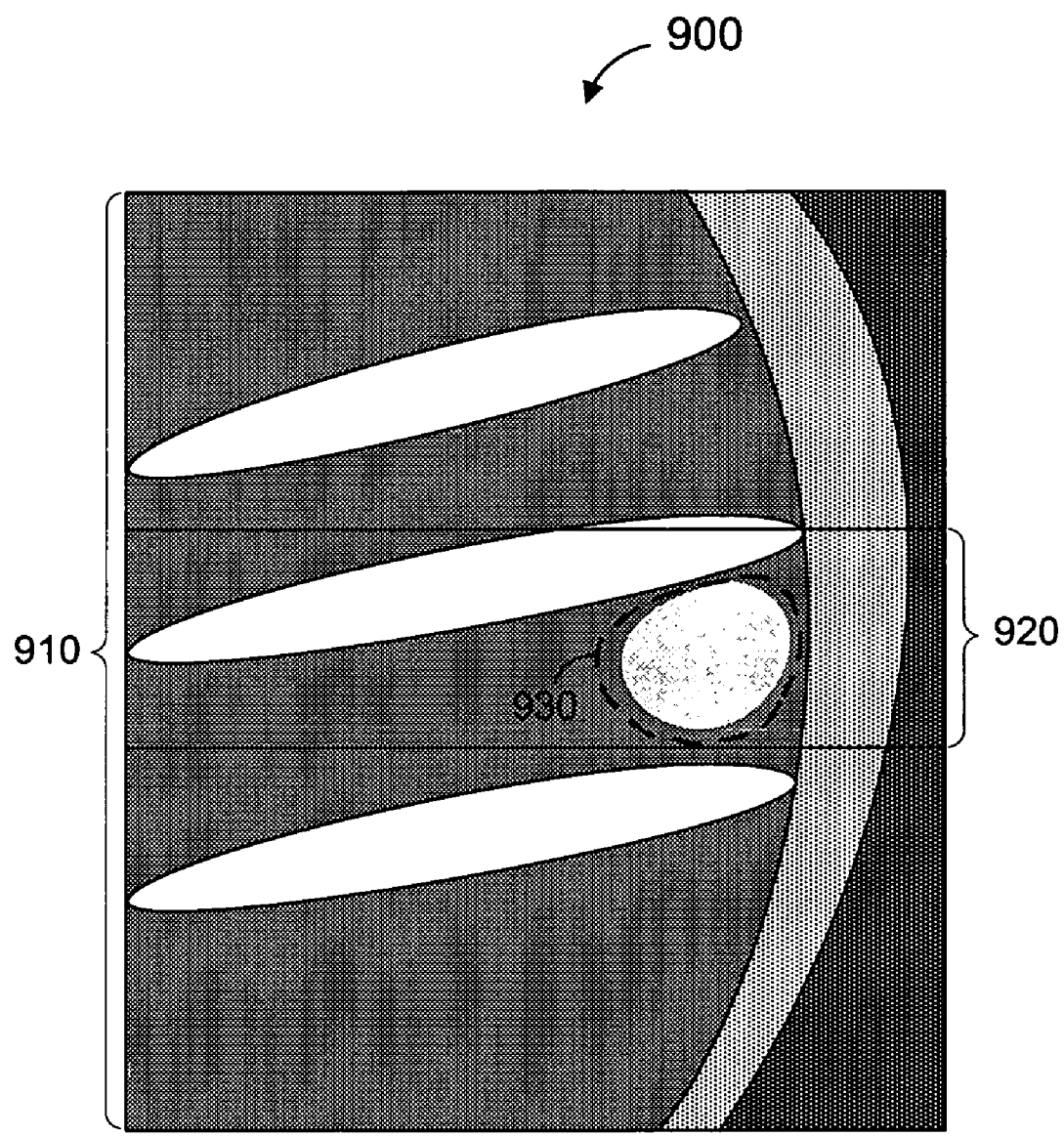
FIG. 9 is a representation of a fluoroscopic image according to some embodiments.

FIG. 9 represents two-dimensional image 900 displayed at S810 according to some embodiments. Image 900 is composed of background image 910 and two-dimensional image 920, boundaries of which are indicated with brackets and solid lines. Image 920 is superimposed on image 910 and is generated at step S809. In some embodiments, characteristics of image 910 and/or image 920 such as contrast, gray level, brightness, etc. may be manipulated prior to step S810 to improve the overall appearance of image 900. Image 900 also includes graphics overlay 930, which may be automatically generated or manually drawn to identify a region of interest in image 900.

Returning to process 800, steps S811 and S812 may be performed substantially in parallel with steps S806 through S810. For example, it is periodically determined at step S811 whether a command has been received to change a Z position of the patient with respect to the X-ray tube. If no such command is received, flow cycles through steps S806 through S810 to acquire new projections, to generate new images based on the acquired projections, and to display the newly-generated images superimposed at corresponding Z positions of the background image.

By virtue of the foregoing, the corresponding Z positions of the background image are periodically updated as time passes. The resulting image 900 may thereby depict motion within these Z positions, while other positions of image 900 remain static. In this regard, overlay 930 may indicate a range of motion of a volume of interest. Other user-definable graphics that are or become known may be overlayed on image 900. These graphics may be used for any suitable purpose, including but not limited to planning and education. Some embodiments allow a user to pause the cycling of process 800 among steps S806 through S810 in order to freeze the two-dimensional image displayed over the background image.

Flow continues from step S811 to step S812 if it is determined that a command has been received to change a Z position of the patient with respect to the X-ray tube. The table is moved at step S812 in accordance with the command, and flow returns to step S806. Accordingly, this movement changes the Z positions at which any subsequently-generated images are superimposed on the selected background image. The subsequently-generated images may therefore depict any motion occurring at the new Z positions. In some embodiments, interactive recursive band pass filtering may be applied to address noise attributable to the depicted motion.

According to some embodiments of process 800, the focal spot is moved in only one direction. In some embodiments, the focal spot is moved in the X-direction to multiple locations and/or in the Z-direction to multiple locations, and projections are acquired corresponding to each focal spot location. Each of these acquired projections may then be used to generate a two-dimensional image at step S810.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
    emitting first electrons from a cathode toward a first focal spot using an X-ray tube located at a first position;
    emitting first radiation from the first focal spot toward an object;
    acquiring a first projection of the object based on the emitted first radiation using a computed tomography radiation detector;
    moving the first focal spot in a first direction to a second focal spot;
    emitting second electrons from the cathode toward the second focal spot using the X-ray tube located at the first position;
    emitting second radiation from the second focal spot toward the object;
    acquiring a second projection of the object based on the emitted second radiation using the computed tomography radiation detector;
    determining a table speed to move the object, wherein the table speed is based on a x-direction sampling rate and a z-direction sampling rate;
    moving the object relative to the X-ray tube in a second direction via a table at the determined table speed, the second direction perpendicular to the first direction;
    emitting third radiation toward the moved object from the first focal spot using the X-ray tube located at the first position;
    acquiring a third projection of the moved object based on the emitted third radiation using the computed tomography radiation detector;
    emitting fourth radiation toward the moved object from the second focal spot using the X-ray tube located at the first position;
    acquiring a fourth projection of the moved object based on the emitted fourth radiation using the computed tomography radiation detector,
    generating an image of the object based on the first projection, the second projection, the third projection and the fourth projection;
    acquiring a two-dimensional image of the object;
    superimposing the image on a portion of the two-dimensional image;
    updating the image using additional projections obtained from the X-ray tube located at the first position; and
    superimposing the updated image on the portion of the two-dimensional image.

2. A method according to claim 1, further comprising:
    rotating an anode during emission of the first electrons, wherein the first electrons impact the anode at a first plurality of locations; and
    rotating the anode during emission of second electrons, wherein the second electrons impact the anode at a second plurality of locations.

3. A method according to claim 1, wherein the first focal spot comprises a first (x,y,z) coordinate, wherein the second focal spot comprising a second (x,y,z) coordinate, and wherein second (x,y,z) coordinate differs from the first (x,y,z) coordinate in at least two of the x-coordinate, the y-coordinate, and the z-coordinate.

4. An apparatus comprising:
    a memory storing processor-executable process steps; and
    a processor in communication with the memory and operative in conjunction with the stored process steps to result in:
    emission of first electrons from a cathode toward a first focal spot using an X-ray tube located at a first position;
    emission of first radiation from the first focal spot toward an object;
    acquisition of a first projection of the object based on the emitted first radiation using a computed tomography radiation detector;
    moving the first focal spot in a first direction to a second focal spot;
    emission of second electrons from a cathode toward the second focal spot using the X-ray tube located at the first position;

emission of second radiation from the second focal spot toward the object;

acquisition of a second projection of the object based on the emitted second radiation using the computed tomography radiation detector;

movement of a focal spot associated with the X-ray tube in a first direction from the first focal spot to the second focal spot;

determination of a table speed to move the object, wherein the table speed is based on a x-direction sampling rate and a z-direction sampling rate;

movement of the object relative to the X-ray tube in a second direction via a table a the determined table speed, the second direction perpendicular to the first direction;

emission of third radiation toward the moved object from the first focal spot using the X-ray tube located at the first position;

acquisition of a third projection of the moved object based on the emitted third radiation using the computed tomography radiation detector;

emission of fourth radiation toward the moved object from the second focal spot using the X-ray tube located at the first position;

acquisition of a fourth projection of the moved object based on the emitted fourth radiation using the computed tomography radiation detector, generating an image of the object based on the first projection, the second projection, the third projection and the fourth projection;

acquisition of a two-dimensional image of the object;

superimposition of the image on a portion of the two-dimensional image;

updating of the image using additional projections obtained from the X-ray tube located at the first position; and superimposition of the updated image on the portion of the two-dimensional image.

5. An apparatus according to claim 4, wherein the first focal spot comprises a first (x,y,z) coordinate, wherein the second focal spot comprising a second (x,y,z) coordinate, and wherein second (x,y,z) coordinate differs from the first (x,y,z) coordinate in at least two of the x-coordinate, the y-coordinate, and the z-coordinate.

6. A system comprising:

an X-ray tube to emit first electrons from a cathode toward a first focal spot while located at a first position, to emit first radiation toward an object from the first focal spot, to emit second electrons from a cathode toward a second focal spot while located at the first position, to emit second radiation toward the object from the second focal spot, and comprising a device to move a focal spot associated with the X-ray tube in a first direction from the first focal spot to the second focal spoil;

a computed tomography detector to acquire a first projection of the object based on the emitted first radiation, and to acquire a second projection of the object based on the emitted second radiation;

a processor to determine a table speed to move the object, wherein the table speed is based on a x-direction sampling rate and a z-direction sampling rate;

a table to move the object relative to the X-ray tube in a second direction at the determined table speed, the second direction perpendicular to the first direction, wherein the X-ray tube is to emit third radiation from the first focal spot toward the moved object while located at the first position, and to emit fourth radiation from the second focal spot toward the moved object while located at the first position, wherein the computed tomography detector is to acquire a third projection of the moved object based on the emitted third radiation, and to acquire a fourth projection of the moved object based on the emitted fourth radiation, wherein the processor is to generate the image of the object based on the first projection, the second projection, the third projection and the fourth projection; and a display to display a two-dimensional image of the object and to display the image superimposed on a portion of the two-dimensional image, wherein the X-ray tube, detector and processor are to update the image while located at the first position, and wherein the display is to display the updated image superimposed on a portion of the two-dimensional image.

7. A system according to claim 6, wherein the first focal spot comprises a first (x,y,z) coordinate, wherein the second focal spot comprising a second (x,y,z) coordinate, and wherein second (x,y,z) coordinate differs from the first (x,y,z) coordinate in at least two of the x-coordinate, the y-coordinate, and the z-coordinate.

\* \* \* \* \*